United States Patent
Peleg et al.

(10) Patent No.: US 10,197,505 B2
(45) Date of Patent: Feb. 5, 2019

(54) METHOD AND SYSTEM FOR LOW COST INSPECTION

(75) Inventors: Ophir Peleg, Moshav Amirim (IL); Zehava Ben Ezer, Moshav Balfuria (IL)

(73) Assignee: CAMTEK LTD., Migdal Haeemek (IL)

( * ) Notice: Subject to any disclaimer, the term of this patent is extended or adjusted under 35 U.S.C. 154(b) by 1485 days.

(21) Appl. No.: 12/673,784

(22) PCT Filed: Aug. 21, 2008
(Under 37 CFR 1.47)

(86) PCT No.: PCT/IL2008/001144
§ 371 (c)(1),
(2), (4) Date: Jan. 19, 2011

(87) PCT Pub. No.: WO2009/024978
PCT Pub. Date: Feb. 26, 2009

(65) Prior Publication Data
US 2011/0164806 A1  Jul. 7, 2011

Related U.S. Application Data

(60) Provisional application No. 60/957,967, filed on Aug. 24, 2007, provisional application No. 60/957,186, filed on Aug. 22, 2007.

(51) Int. Cl.
*G01N 21/95* (2006.01)
*G01N 21/88* (2006.01)
*H01L 21/66* (2006.01)

(52) U.S. Cl.
CPC . *G01N 21/9501* (2013.01); *G01N 2021/8822* (2013.01); *H01L 22/12* (2013.01)

(58) Field of Classification Search
CPC ........ G06T 15/506; G06T 2207/10024; G06K 9/4661
USPC .................................................. 382/141, 152
See application file for complete search history.

(56) References Cited

U.S. PATENT DOCUMENTS

| | | | |
|---|---|---|---|
| 5,949,900 A * | 9/1999 | Nakamura et al. ........... 382/145 |
| 6,621,568 B1 * | 9/2003 | Yonezawa .................. 356/237.2 |
| 6,788,411 B1 * | 9/2004 | Lebens ......................... 356/394 |
| 2003/0039388 A1 * | 2/2003 | Ulrich et al. ................. 382/145 |
| 2004/0184653 A1 * | 9/2004 | Baer et al. .................... 382/145 |

* cited by examiner

*Primary Examiner* — Edward Park
(74) *Attorney, Agent, or Firm* — Raches Patents

(57) ABSTRACT

A method for macro inspection, the method includes: (i) concurrently illuminating a current group of spaced apart object sub areas; wherein light reflected in a specular manner from a certain object sub area of the current group of object sub areas is expected to be detected by a certain sensor element of a current group of spaced apart sensor elements that correspond to the current group of spaced apart object sub areas; wherein the object sub areas are spaced apart so as to reduce a probability of a detection of non-specular light from the object; wherein each image sub area comprises multiple pixels; (ii) obtaining image information from the current group of spaced apart sensor elements; and (iii) processing at least a portion of the image information to provide an inspection result.

29 Claims, 20 Drawing Sheets

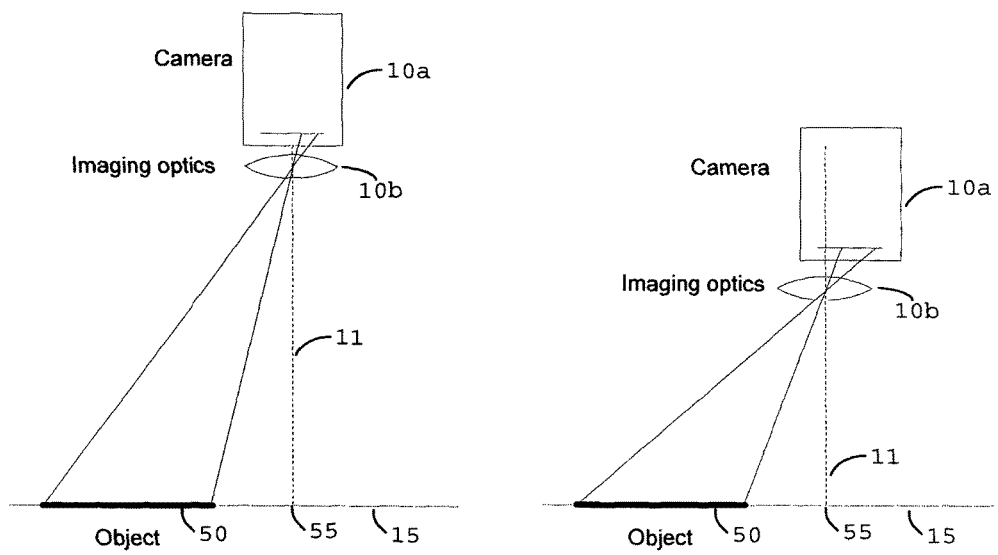
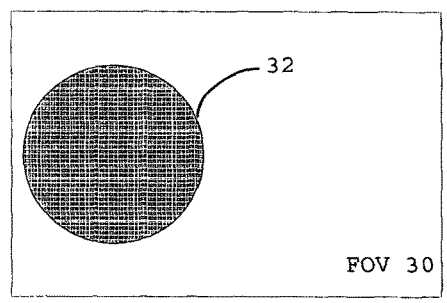
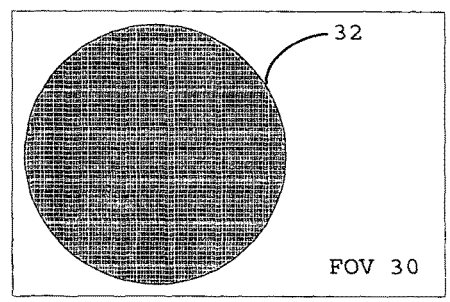
Concentric optics
Figure 4a
Non-concentric optics
Figure 4b Illuminating a curved diffusive reflecting surface by light beams generated by a first illumination source. The curved diffusive reflecting surface is shaped and positioned so as to direct at least some of the light beams towards the wafer. 2110

Collecting, by an imaging device, light beams that were reflected from the wafer. The imaging device is positioned so as to reduce a probability of collecting a reflection of the imaging device. 2120

Dark field illuminating the wafer. 2130

Collecting, by an imaging device, light beams from the wafer. The imaging device is positioned so as to reduce a probability of collecting a reflection of the imaging device. 2140

METHOD AND SYSTEM FOR LOW COST INSPECTION

RELATED APPLICATIONS

This application is a National Phase Application of PCT International Application No. PCT/IL2008/001144, International Filing Date Aug. 21, 2008, which in turn claims priority of Provisional Patent Applications, 60/957,967, filed Aug. 21, 2007 and 60/957,186, filed Aug. 22, 2007, all being incorporated herein in their entirety.

BACKGROUND OF THE INVENTION

There is available equipment for wafer optical inspection to detect defects on the front-side surface and/or backside. In general, such equipment is using optical microscopic image capture, where the defects are detected in high to medium resolution (such as the Falcon inspection system of Camtek Ltd., Israel). Another approach is laser scan, where irregularities in the scattering pattern are detected as defects.

The above systems and methods illuminate the wafer by a small spots of light and utilize high resolution optics, highly accurate mechanics (including precise X, Y or R-theta stages) and powerful processors. This increases the cost of these systems.

There is a growing need to provide low cost inspection system that will be able to detect "global" phenomena such as lack of photoresist, contamination and the like.

There is a growing need to provide low cost inspection system that will be able to detect "global" phenomena such as overall contamination of a backside of a wafer.

SUMMARY

A method for macro inspection, the method includes: concurrently illuminating a current group of spaced apart object sub areas; wherein light reflected in a specular manner from a certain object sub area of the current group of spaced apart object sub areas is expected to be detected by a certain sensor element of a current group of spaced apart sensor elements that correspond to the current group of spaced apart object sub areas; wherein the spaced apart object sub areas are spaced apart so as to reduce a probability of a detection of non-specular light from the object; obtaining image information from the current group of spaced apart sensor elements; wherein the image information includes multiple spaced apart image sub areas; wherein each image sub area includes multiple pixels; and processing at least a portion of the image information to provide an inspection result.

The object sub areas are spaced apart by at least one half a width of an object sub area.

The method can include activating a current group of spaced apart illumination elements so as to concurrently illuminate the current group of spaced apart object sub areas.

The method can include obtaining image information from another group of spaced apart sensor elements that differ from the current group of spaced apart sensor elements.

The method can include: selecting a next group of spaced apart object sub areas; concurrently illuminating the next group of spaced apart object sub areas; wherein light reflected in a specular manner from a certain sub area of the next group of spaced apart object sub areas is expected to be detected by a certain sensor element of a next group of spaced apart sensor elements that correspond to the next group of spaced apart object sub areas; wherein the object sub areas are spaced apart so as to reduce a probability of a detection of non-specular light from the object; obtaining image information from the next group of spaced apart sensor elements; and processing at least a portion of the image information to provide an evaluation of the object.

The method can include repeating the selection of next group of spaced apart object sub areas until obtaining image information from an entire continuous area of the object.

The entire continuous area of the object is a portion of the object; and wherein the method can include introducing a mechanical movement between the object and the sensor and repeating the stages of concurrently illuminating, obtaining image information and selecting a next group of spaced apart object sub areas until obtaining image information from another entire continuous area of the object.

The method can include repeating the selection of next group of spaced apart object sub areas until obtaining image information from the entire object.

The method can include selecting illuminating elements of a screen, and activating the selected elements of the screen so as to illuminate a current group of spaced apart object sub areas. The screen can be an LCD screen, a plasma screen or other screen. The screen can be followed by a diffuser.

Each image sub area can include multiple pixels each representing an object element of about 0.1 mm by 0.1 mm.

The method can include obtaining image information by an imaging system that includes imaging optics and a imaging sensor; wherein an optical axis of the imaging optics intersects an imaging surface of the imaging sensor at a point that differs from a center of the imaging sensor.

A method for illuminating a wafer, the method includes: illuminating a curved diffusive reflecting surface by light beams generated by a first illumination source; wherein the curved diffusive reflecting surface is shaped and positioned so as to direct at least some of the light beams towards the wafer; collecting, by an imaging device, light beams that were reflected from the wafer; wherein the imaging device is positioned so as to reduce a probability of collecting a reflection of the imaging device.

The method can include illuminating a backside of the wafer.

The method can include collecting light beams by an imaging device that has an optical axis that is tilted in relation to the wafer by a tilt angle that differs than ninety degrees.

The curved diffusive reflecting surface can have an imaginary central axis that is tilted in relation to the wafer by a tile angle that differs from ninety degrees.

The method can include positioning the wafer and an objective lens of an imaging device near opposite ends of the curved diffusive reflecting surface.

The method can include dark field illuminating the wafer.

A system for macro inspection, the system includes: illumination device configured to concurrently illuminate a current group of spaced apart object sub areas; wherein light reflected in a specular manner from a certain object sub area of the current group of object sub areas is expected to be detected by a certain sensor element of a current group of spaced apart sensor elements that correspond to the current group of spaced apart object sub areas; wherein the object sub areas are spaced apart so as to reduce a probability of a detection of non-specular light from the object; an imaging device configured to obtain image information from the current group of spaced apart sensor elements wherein the image information includes multiple image sub areas, each image sub area includes multiple pixels; and a processor configured to process at least a portion of the image information to provide an inspection result.

The object sub areas are spaced apart by at least one half a width of an object sub area.

The illumination device can be configured to activate a current group of spaced apart illumination elements so as to concurrently illuminate the current group of spaced apart object sub areas.

The system can be configured to obtain image information from another group of spaced apart sensor elements that differ from the current group of spaced apart sensor elements.

The system can be configured to select a next group of spaced apart object sub areas; concurrently illuminate the next group of spaced apart object sub areas; wherein light reflected in a specular manner from a certain object sub area of the next group of spaced apart object sub areas is expected to be detected by a certain sensor element of a next group of spaced apart sensor elements that correspond to the next group of spaced apart object sub areas; wherein the object sub areas are spaced apart so as to reduce a probability of a detection of non-specular light from the object; obtain image information from the next group of spaced apart sensor elements; and process at least a portion of the image information to provide an evaluation of the object.

The system can be configured to repeat the selection of next group of spaced apart object sub areas until obtaining image information from an entire continuous area of the object.

The entire continuous area of the object is a portion of the object; and wherein the system can include a mechanical stage for introducing a mechanical movement between the object and the sensor and the system is configured to repeat a concurrent illumination, image obtaining and process of at least a portion of the image information and select a next group of spaced apart object sub areas until obtaining image information from another entire continuous area of the object.

The system can be configured to repeat the selection of a next group of spaced apart object sub areas until obtaining image information from the entire object.

The illuminating device can include a screen and the system can select illuminating elements of the screen to be activated so as to illuminate a current group of spaced apart object sub areas. The screen can be an LCD screen, a plasma screen or other screen. The screen can be followed by a diffuser.

The system can include an imaging system that includes imaging optics and an imaging sensor. The optical axis of the imaging optics can intersect an imaging surface of the imaging sensor at a point that differs from a center of the imaging sensor.

The system can be configured to illuminate object sub areas that are imaged to provide image sub areas wherein each sub area includes multiple pixels each representing an object element of about 0.1 mm by 0.1 mm.

A system for illuminating a wafer, the system includes a first illumination source; a curved diffusive reflective surface; and an imaging device; wherein the first illumination source illuminates the curved diffusive reflecting surface; wherein the curved diffusive reflecting surface is shaped and positioned so as to direct at least some of the light beams towards the wafer; wherein the imaging device collects light beams that were reflected from the wafer; wherein the imaging device is positioned so as to reduce a probability of collecting a reflection of the imaging device.

The curved diffusive reflective surface directs light beams towards a backside of the wafer.

The optical axis of the imaging device is tilted in relation to the wafer by a tilt angle that differs than ninety degrees.

The curved diffusive reflecting surface has an imaginary central axis that is tilted in relation to the wafer by a tile angle that differs from ninety degrees.

The system curved diffusive reflecting surface had two opposite ends—the wafer is positioned near one end while an objective lens of an imaging device is positioned near the other end.

The system can include dark field illumination source.

BRIEF DESCRIPTION OF THE INVENTION

The present invention will be understood and appreciated more fully from the following detailed description taken in conjunction with the drawings in which:

FIG. 4 illustrates systems and images of an object according to various embodiments of the invention;

FIGS. 20-21 illustrate methods according to various embodiments of the invention.

DETAILED DESCRIPTION OF THE DRAWINGS

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

According to an embodiment of the invention a low cost macro inspection systems and methods are provided. According to an embodiment of the invention a low cost backside inspection systems and methods are provided.

A flat and shiny object such as a wafer can be illuminated and imaged to provide one or more images. In other words the field of view can include the whole wafer or a large portion of the wafer.

By using very large pixels (each representing an object element of about 0.1 mm by 0.1 mm or more) and using optics that have limited resolution macro defects (or other macro phenomena such as process variations) can be detected without using expensive hardware (including optics, mechanical stages and processors).

Such a low cost system can be used in incoming or out-coming inspection of wafers in the back end & packaging process or for the sake of track integrated excursion monitor of macro defects along the track steps. Multiple systems can be integrated in an in-line manner into the manufacturing lines.

To achieve a bright-field image of a specular type and large area object in a single or very small number of image grabs (on the contrary to a line or area scanner), the illumination device should be large enough (larger than the object in each grab) and homogeneous, thus providing light rays within such angles that would be reflected from the object in a specular way towards the imaging device.

In that case, the imaging device should be moved away from the object such that it would not be self-reflected to appear as part of the image (an exception is when a beam-splitter is used, which is more complicated for implementation).

Figure 1A:
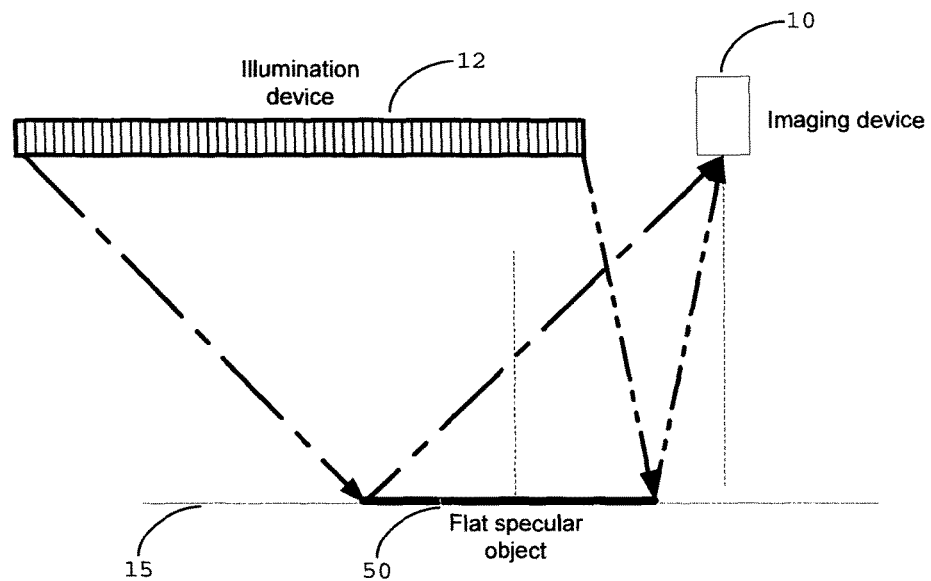
FIGS. 1a, 1b, 2a, 2b, 5, 6 and 7 illustrates systems and inspected objects according to various embodiments of the invention.
Figure 1B:
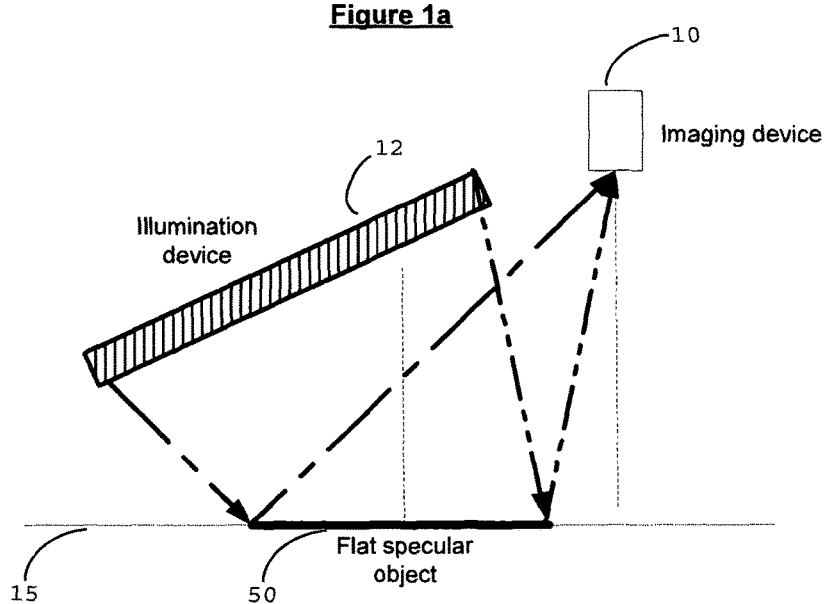

According to one embodiment the optical axis of the imaging device is vertical to the flat object plane. This configuration is illustrated in FIGS. 1a and 1b. The optical axis 11 of imaging device 10 crosses the object plane 15 outside the boundaries of the object 50 in order to avoid self-reflection. Object 50 is imaged non-symmetrically in respect to the optical axis 11 of imaging device 10. In FIGS. 1a and 1b the optical axis 11 of imaging device 10 is perpendicular to object 50. In FIG. 1a the illumination device 12 is parallel to object 50 while in FIG. 1b the optical axis 11 of imaging device 10 is tilted in relation to object 50.

Figure 2A:
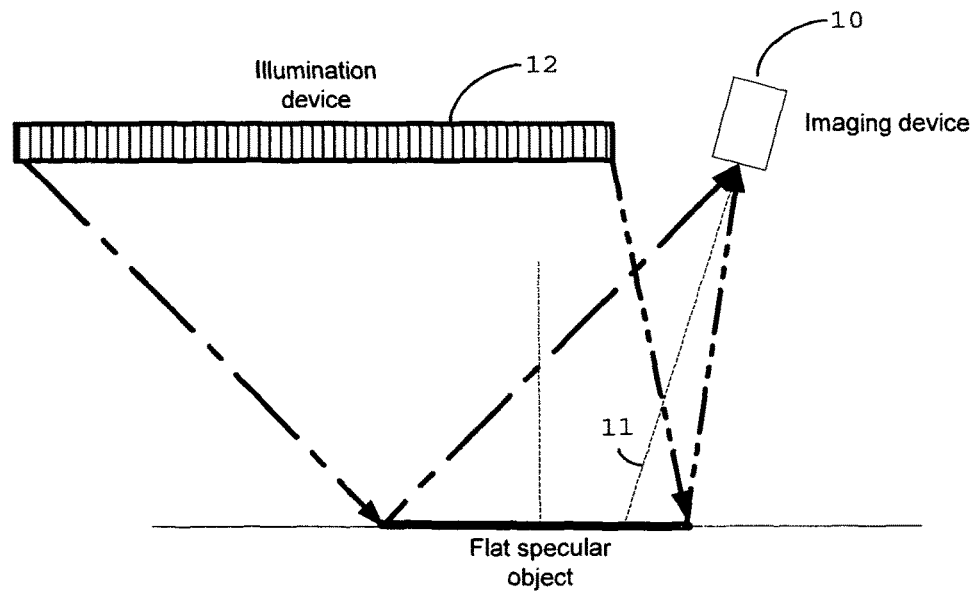
Figure 2B:
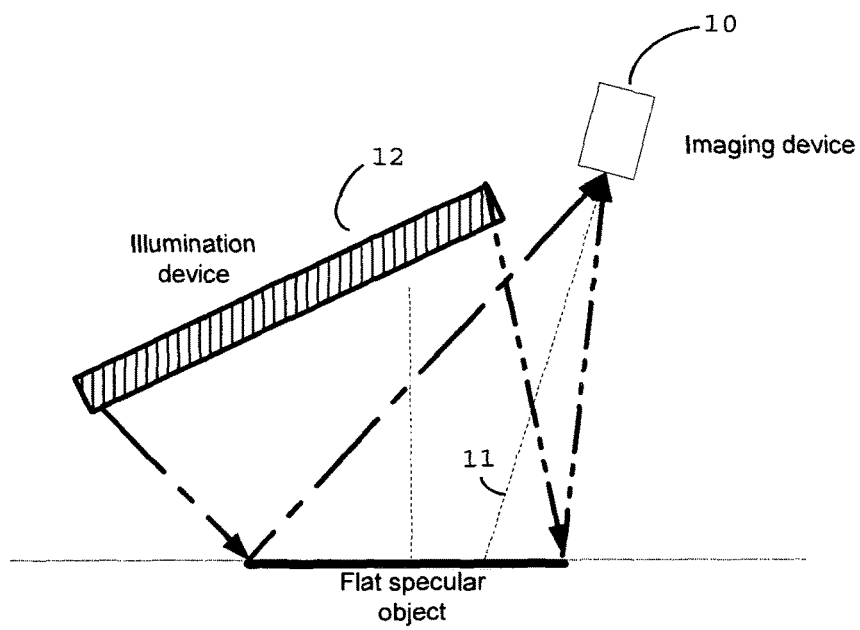

According to one embodiment of the invention the optical axis of the imaging device is inclined (not vertical) in relation to the flat object plane. This configuration is illustrated in FIGS. 2a and 2b. In FIGS. 2a and 2b the optical axis 11 of imaging device 10 is inclined (not perpendicular) to object 50. In FIG. 2a the illumination device 12 is parallel to object 50 while in FIG. 2b the optical axis 11 of imaging device 10 is tilted in relation to object 50.

If the imaging device is not parallel to the flat object plane then the optical axis of the imaging device may cross the object plane inside or outside of the object boundaries to avoid self-reflection. The object is imaged non-symmetrically in respect to the optical axis of the imaging device.

Figure 3A:
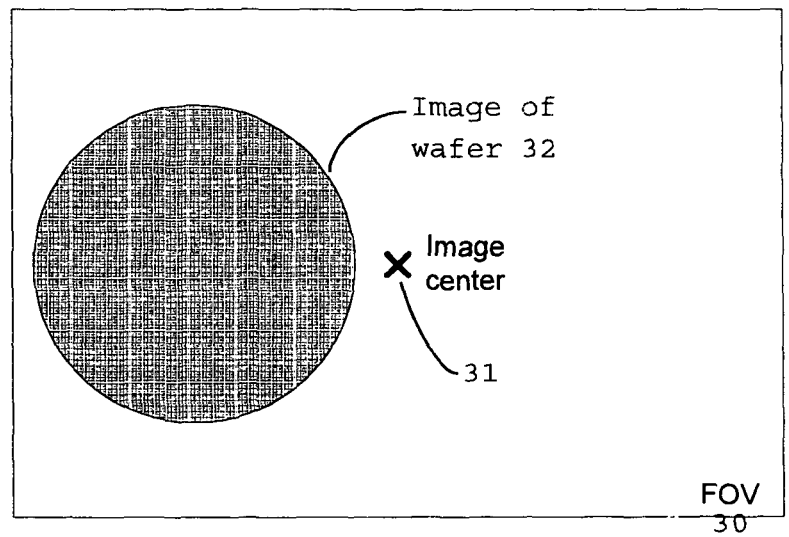
FIGS. 3a and 3b illustrate images of an object according to various embodiments of the invention.
Figure 3B:
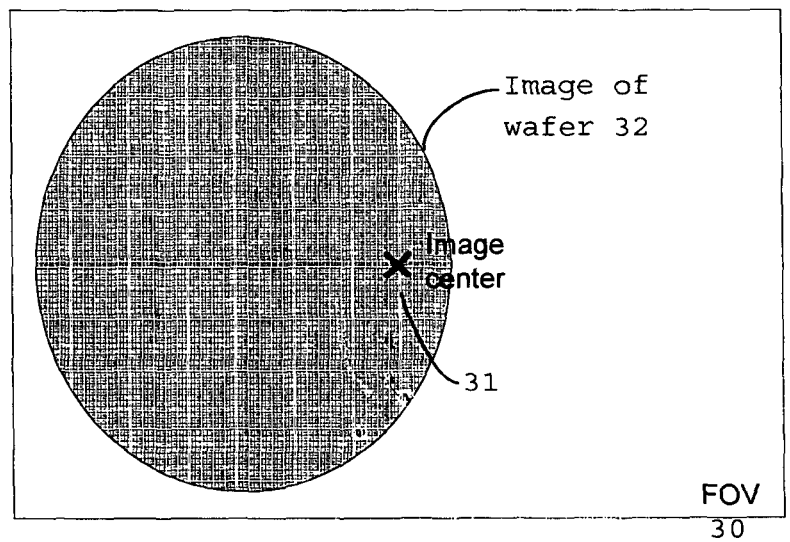

An imaging device can include a camera (also referred to as sensor) and imaging optics. The optical axis of the imaging optics can coincide with the optical axis of the camera. If this relationship is maintained, if the optical axis of the imaging optics is normal to the object, and if the entire image of the object should be within the field of view of the camera then the entire image should be included within less than half of the field of view of the camera. The configuration of FIG. 1a can provide the outcome illustrated in FIG. 3a while the configuration of FIG. 1b can provide the outcome illustrated in FIG. 3b. FIG. 3a illustrates an image 32 of a circular object (such as a wafer) that is included within less than a half of field of view (FOV) 30 of imaging device 10. The center point 31 of FOV 30 is outside image 32. FIG. 3b illustrates image 32 of the circular object that is included within a field of view (FOV) 30 of imaging device 10. The center point of FOV 30 is within image 32.

Thus, for a given optical configuration (object size, imaging optics and camera frame and pixels properties) and when maximizing the size of the object image without getting self-reflection, the potential geometric resolution in the vertical configuration is smaller than the potential geometric resolution in the inclined configuration.

Imaging device 10 can include camera 10a (or other type of imaging sensor) and imaging optics 10b. These are illustrated in FIGS. 4a and 4b. FIGS. 4a and 4b illustrate two configurations in which the optical axis of the imaging optics is positioned such as to intersect (at intersection point 55) with the object plane 15 outside object 50.

In one embodiment of the invention, the imaging optics is positioned so that its optical axis is translated relatively to the center of camera frame (the center of the sensing area of the imaging sensor). Assuming that the imaging optics field-of-view (FOV) is not limited to the camera frame size, then in the vertical configuration (when the optical axis of the camera is perpendicular to the object) the camera frame can be utilized more optimally to capture the entire object in the image with an increased resolution but substantially without distortion—as illustrated by FIG. 4b. FIGS. 4a and 4b illustrate the FOV 30 of camera 10a and the image of object 32. While FIG. 3b is obtained by tilting the optical axis of the camera in relation to the object plane, FIG. 4b is obtained while maintaining a vertical relationship between the optical axis and the object plane.

To capture a bright-field image of an entire specular object in a single grab, the illumination device should illuminate each and every point of the object in a specular way relatively to the imaging module. To achieve that, the illumination device should have a large illumination area with extended angular distribution, where at least a subset of its illuminating points are illuminating all the object points, where each illuminating point is correlated to an object point by a specular light ray.

By doing that, a brightfield image is received. Features with color information and others such that stains, edge defects (e.g. chipping) are well detected. However, other features, such as particles, certain type of scratches and other three dimensional perturbation may not be detected with high contrast. This type of features may have characteristics of scattering centers, thus light rays that are scattered from them and that are captured by the imaging module are not only the specular rays.

Figure 5:
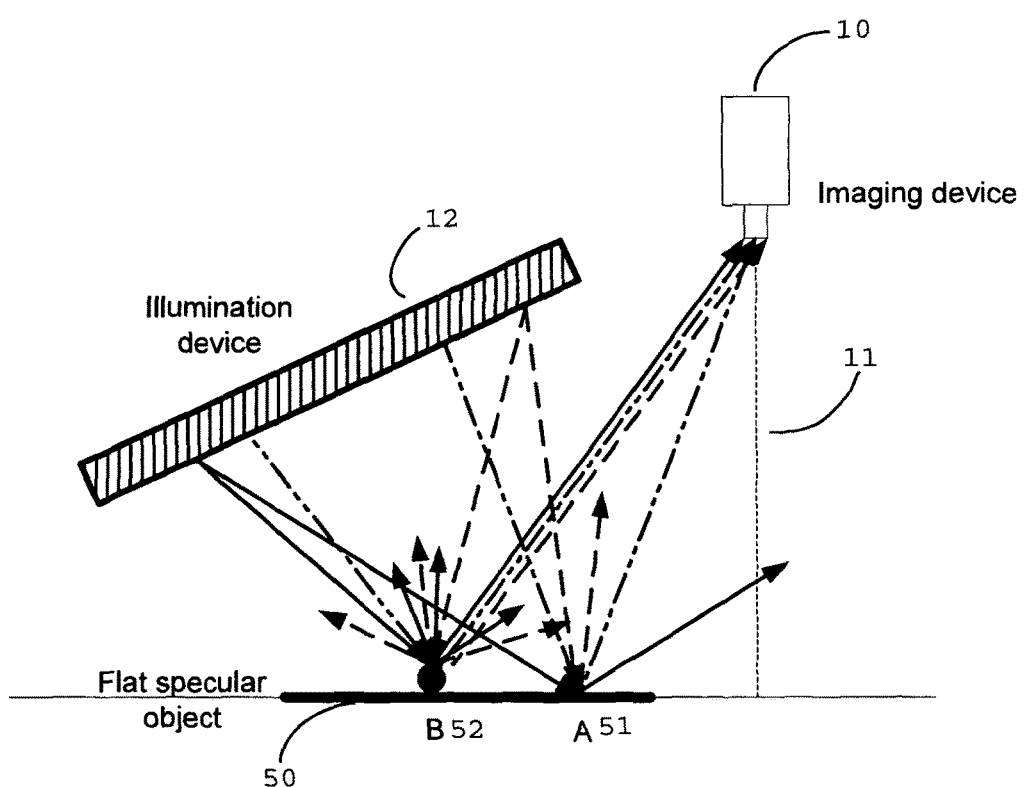

FIG. 5 illustrates an illumination of an object that includes point A 51 and point B 52. Object 50 is illuminated by a large area light source. Point A 51 of the object is specular, thus only the specular rays (with narrow angular distribution that is correlated to the imaging module numerical aperture) are captured by the imaging device 10 to create a bright point in the image. These rays are enclosed within a narrow cone of light emerging from a single point surrounding of the illumination area.

Point B 52 of the object is a scattering center type. Thus, all light rays that hit point B 52 and which are emerging from the whole illumination area are contributing some reflected light that is scattered in the direction of imaging device 10 to create another bright point in the image. The intensity contrast between points A and B 51 and 52 is very low if any. The reason for that is that pure brightfield imaging (point A) is mixed with partial darkfield imaging (Point B).

The following illumination systems and methods are suggested to achieve higher contrast between specular points (e.g. type A) to scattering points (e.g. type B) or non horizontal specular points (type C).

Figure 6:
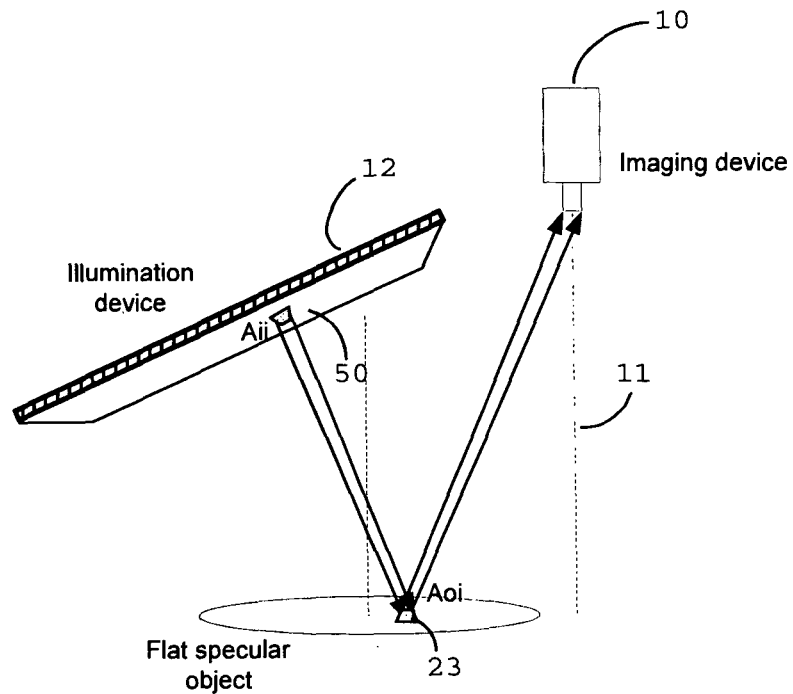

An object area is virtually divided into small object sub areas ($Ao_i$) each small sub area includes multiple pixels—each pixels is at least few tens of microns wide. Each object sub area is correlated to (associated with) an illumination sub area ($Ai_i$) of illumination device 12, such that the illumination sub area ($Ai_i$) illuminates the object sub area ($Ao_i$) by almost solely specular light rays relatively to the imaging module. In FIG. 6 illumination sub area $Ai_i$ 13 illuminates object sub area ($Ao_i$) 23 so that imaging device 10 receives reflected light rays from object sub area ($Ao_i$) and does not (or does not receive a substantially amount)

receive scattered (darkfield) light. In other words—object sub area ($Ao_i$) is more purely brightfield illuminated and not (or almost not) darkfield illuminated. An illumination sub area can include one or more illumination elements.

Figure 7:
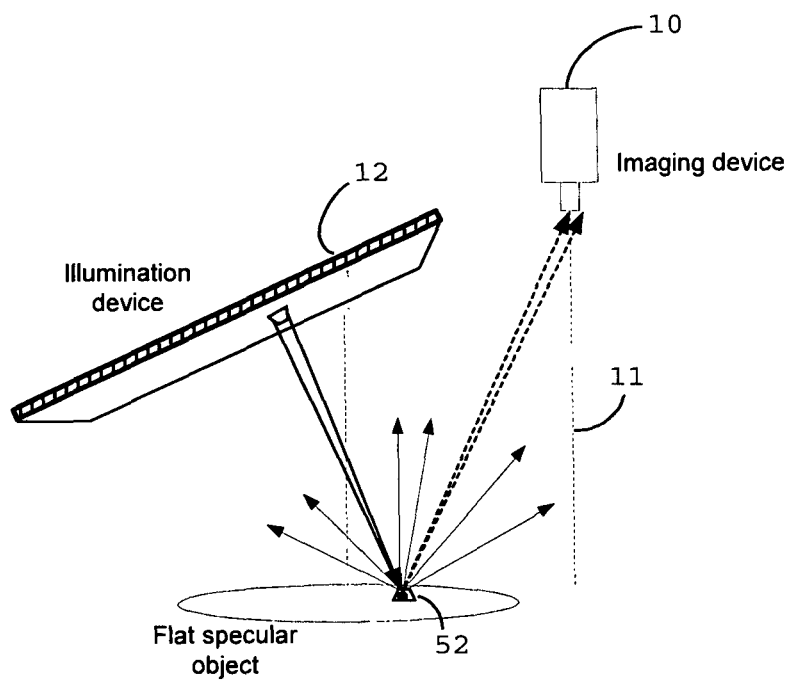

If the object sub area is flat and specular, then its illumination by bright field illumination will result in a brightfield image of that illuminate object sub area. If the object sub area includes scattering points (such as scattering point 52 of FIG. 7) or non-horizontal specular points, these would alter the reflection direction relatively to specular reflection and these points would be imaged as darker points. This way, the contrast between a non-specular points (that may be classified as defects in the object) to the specular image sub area is improved.

In order to generate a full image of the object, multiple object sub areas should be illuminated, one object sub area after the other. Different object sub areas can overlap. At each iteration the respective portions of the image that correlates to the particular object sub area ($Ao_i$) are cropped (out of the field of view that includes the entire illuminated area of the object) to create an image section ($Is_i$) which is also referred to as image sub area. All cropped image sections ($Is_i$) are then attached together aside each other to generate the image of the entire object or an entire continuous area of the object.

Figure 8:
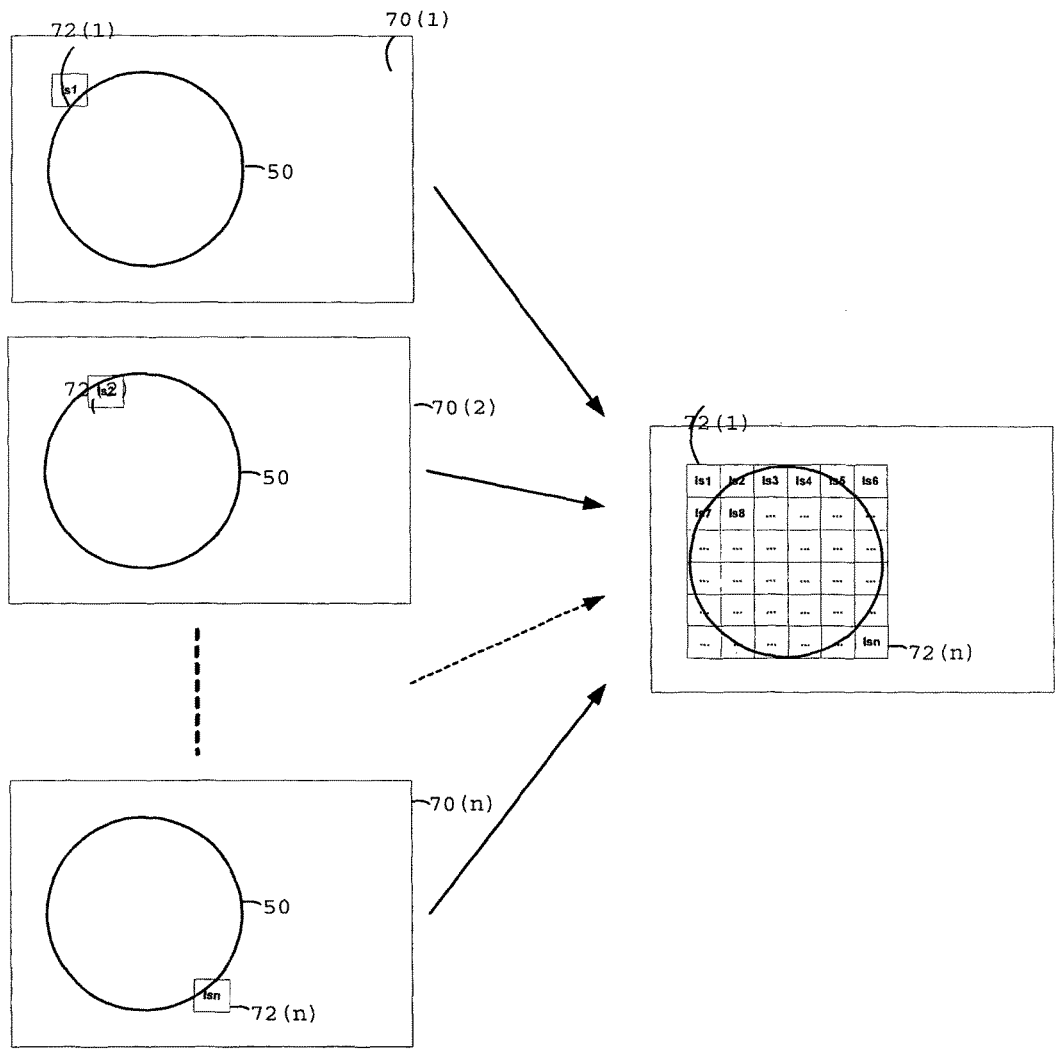
FIGS. 8-10 illustrate image processing according to various embodiments of the invention.

FIG. 8 illustrates object 50 as being illuminated multiple (n) times, wherein during each time image information relating to a single object sub area (this image information is also referred to as image sub area) is taken into account. Thus, images 70(1)-70(n) are processed by cropping the n'th image sections 70(1)-70(n), each including a single image section (image sub area) Is1-Isn that corresponds to a single object sub area. The above procedure may require quite many images to be captured previously to the final image generation.

In one embodiment of the invention, a group of the illumination sub areas are activated concurrently in order to illuminate by a specular mode a group of spaced apart object sub areas. The object sub areas are separated from each other by a gap that can be a fraction of an object sub area or more than an object sub area. Conveniently, the gap is about half the size of each object sub area or more. Accordingly—a group of spaced apart object sub areas are illuminated by a group of spaced apart illumination sub areas.

By concurrently illuminating groups of object sub areas only a few iterations (few acquired images) would enable generation of final image and will assure that substantially no near darkfield rays are detected in the image of each original sub area. In many cases it is close enough to generating an image by the single sub area position-changing mode.

Figure 9:
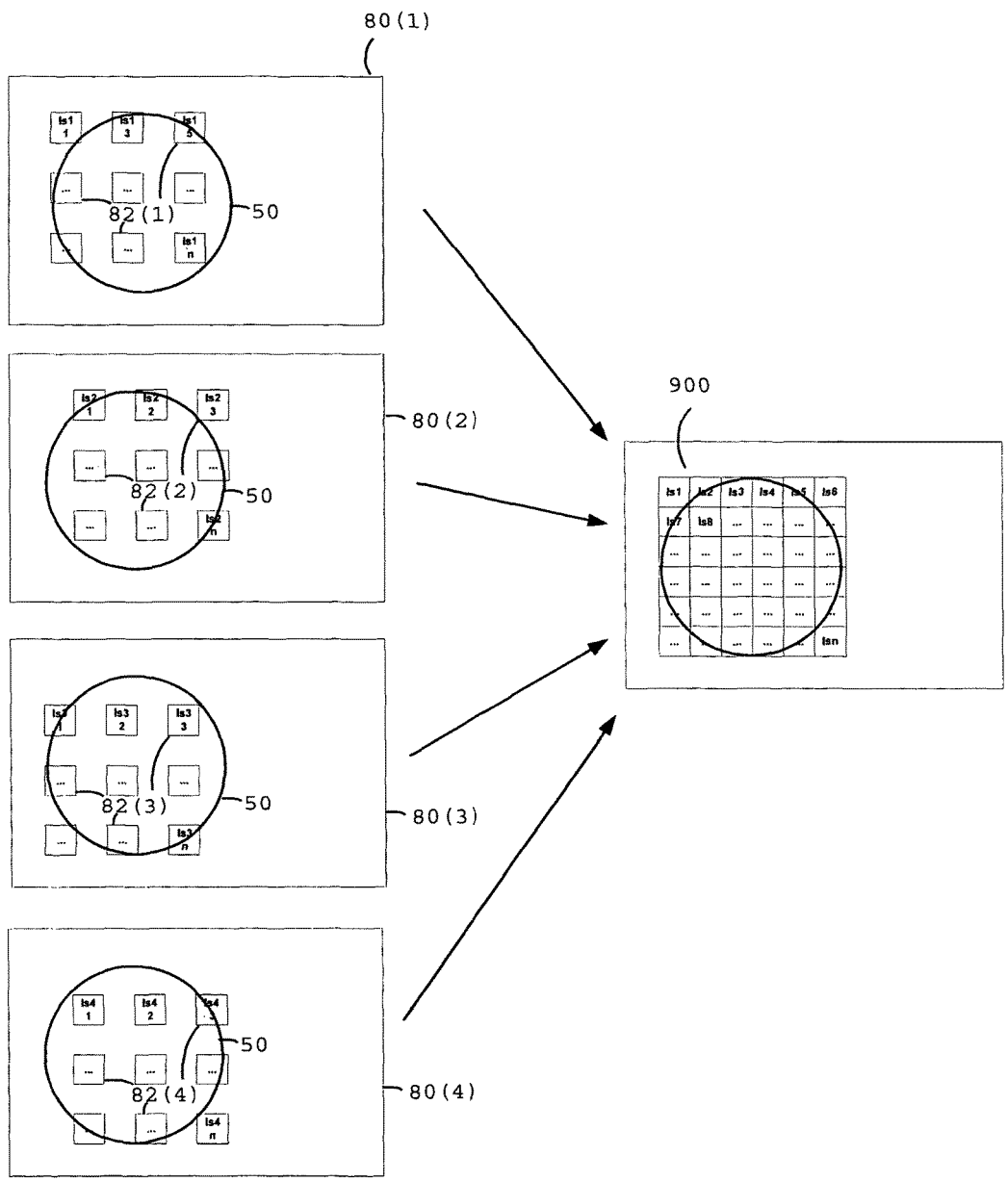

FIG. 9 presents an example of this mode of image generation by four groups of sub areas.

FIG. 9 illustrates four iterations of illumination during which four different groups of spaced apart sub areas of object 50 are illuminated by corresponding groups of spaced apart illumination sub areas. During each iteration the respective sections in each image that correlates to the particular group of object sub areas ($Ao_i$) are cropped and finally combined together to generate the final image.

Image 80(1), acquired during a first iteration, includes image sections Is1,1, Is1,3, Is1,5 . . . Is1,n (collective denoted 82(1)) that includes bright field information of a first group of spaced apart object sub areas.

Image 80(2), acquired during a second iteration, includes image sections Is2,1, Is2,2, Is2,2 . . . Is2,n (collective denoted 82(1)) that includes bright field information of a second group of spaced apart object sub areas that differs from the first group of spaced apart object sub areas.

Image 80(3), acquired during a third iteration, includes image sections Is3,1, Is3,3, Is3,5 . . . Is3,n (collective denoted 82(3)) that includes bright field information of a third group of spaced apart object sub areas that differs from the mentioned above groups of spaced apart object sub areas.

Image 80(4), acquired during a fourth iteration, includes image sections Is4,1, Is4,2, Is4,3 . . . Is4,n (collective denoted 82(4)) that includes bright field information of a group of spaced apart object sub areas that differs from the mentioned above groups of spaced apart object sub areas.

All these image sections are combined to provide an image 900 that includes Is1 . . . Isn.

The groups of sub areas may overlap to some extent and the cropping may cut smaller sections than the illuminating sub areas as long as the final combination generates a whole brightfield image of the object.

In another embodiment of the invention the inter gaps of sub areas are cropped to give a darkfield image. The object sub areas that are not illuminated by the illumination sub areas, but surround the (specular illuminated) spaced apart object sub areas, are illuminated by (mostly near) darkfield rays. Some features (e.g. defects) are seen more clearly by darkfield illumination mode.

Figure 10:
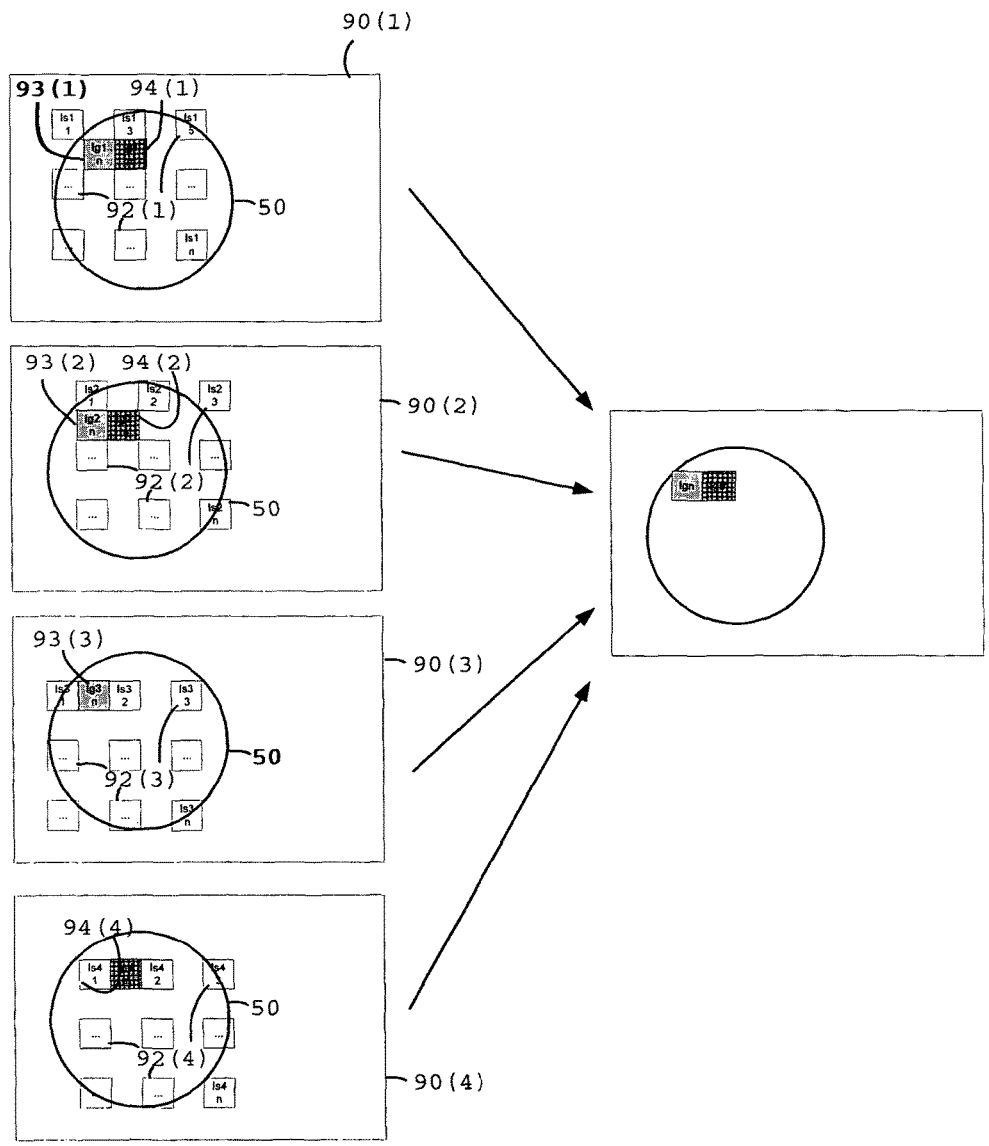

FIG. 10 shows an example of one case of four sub areas groups, where two image information obtained from gaps between object sub areas that are brightfield illuminated are cropped out of the 4 original images to be added to a darkfield image of the object.

Image 90(1), acquired during a first iteration, includes image sections Is1,1, Is1,3, Is1,5 . . . Is1,n (collective denoted 82(1)) that includes bright field information of a first group of spaced apart object sub areas. Image 90(1) also includes multiple dark field image sections such as darkfield image section Ig1n 93(1) and Ig1m 94(1) that include light scattered from object sub areas that were not included in the first group of spaced apart object sub areas.

Image 90(2), acquired during a second iteration, includes image sections Is2,1, Is2,2, Is2,2 . . . Is2,n (collective denoted 82(1)) that includes bright field information of a second group of spaced apart object sub areas that differs from the first group of spaced apart object sub areas. Image 90(1) also includes multiple dark field image sections such as darkfield image section Ig1n 93(1) and Ig1m 94(1) that include light scattered from object sub areas that were not included in the first group of spaced apart object sub areas. Image 90(2) also includes multiple dark field image sections such as darkfield image section Ig2n 93(2) and Ig2m 94(2) that include light scattered from object sub areas that were not included in the second group of spaced apart object sub areas.

Image 90(3), acquired during a third iteration, includes image sections Is3,1, Is3,3, Is3,5 . . . Is3,n (collective denoted 82(3)) that includes bright field information of a third group of spaced apart object sub areas that differs from the mentioned above groups of spaced apart object sub areas. Image 90(3) also includes multiple dark field image sections such as darkfield image section Ig3n 93(3) that include light scattered from object sub areas that were not included in the third group of spaced apart object sub areas.

Image 90(4), acquired during a fourth iteration, includes image sections Is4,1, Is4,2, Is4,3 . . . Is4,n (collective denoted 82(4)) that includes bright field information of a group of spaced apart object sub areas that differs from the mentioned above groups of spaced apart object sub areas.

Image 90(4) also includes multiple dark field image sections such as darkfield image section Ig4m 94(4) that include light scattered from object sub areas that were not included in the fourth group of spaced apart object sub areas.

All these darkfield image sections can be combined to provide an image that includes darkfield image sections.

The illumination of different groups of spaced apart object sub areas requires a configurable illumination device or a combination of an illumination device and a configurable spatial filter or even a combination of configurable illumination device and a configurable spatial filter. The illumination device may also have the ability to adjust the light intensity and to illuminate by varying spectral distribution of light (different colors of light).

The illumination device may be an LCD screen. A diffuser is placed between the LCD screen and the object and especially is placed in very close proximity to the LCD screen in order to diffuse the singularity of the individual LCD cells, which otherwise may interfere with the image. Processor and a display board control the screen to feed the different displayed patterns. The patterns may be very quickly exchanged (due to the fast response of an LCD screen). The patterns may be designed to illuminate with controlled duration, intensity, colors and shapes.

The system can illuminate and acquire images of the entire object (or rather groups of spaced apart object sub areas that are spread over the entire object) but this is not necessarily so. For example, the system can illuminate and acquire images of only a section if the object (or rather groups of spaced apart object sub areas that are spread over a section of the object) at a time. In the latter case mechanical movement can be introduced between the object and the illumination optics in order to change the object section that is being reviewed. The latter configuration allows using a more compact illumination and imaging arrangement. The latter configuration can provide better resolution in relation to the former configuration—if the same camera is used.

An example of this configuration is a circular object (e.g. a wafer) that is placed on a rotating stage. The stage rotates by a certain angle to change the object position. As an example, the object is captured in four sections, each section includes about a quarter of the wafer. In that case the stage rotates by 90° between each quarter capture. The previous procedures of generating a brightfield image and a darkfield image are implemented for each quarter and finally the four images are combined to create the whole object image.

In one embodiment of the invention the brightfield illumination device is a section of diffusive reflecting conic surface. This embodiment is disclosed in FIGS. 11-19. The surface is illuminated by an external illumination source, which is not directly illuminating the object. The reflected light from the diffusive surface is illuminating the flat object to create a brightfield image of the object (but not pure bright).

In another embodiment of the invention there may be implemented oblique darkfield illumination. The illumination sources are positioned with an inclination of shallow angle relatively to the object plane.

This configuration of darkfield imaging is suitable for imaging objects such as un-patterned wafers or wafer backside.

In one embodiment of the invention the brightfield illumination device is a section of diffusive reflecting curved (substantially conic) surface.

Figure 11:
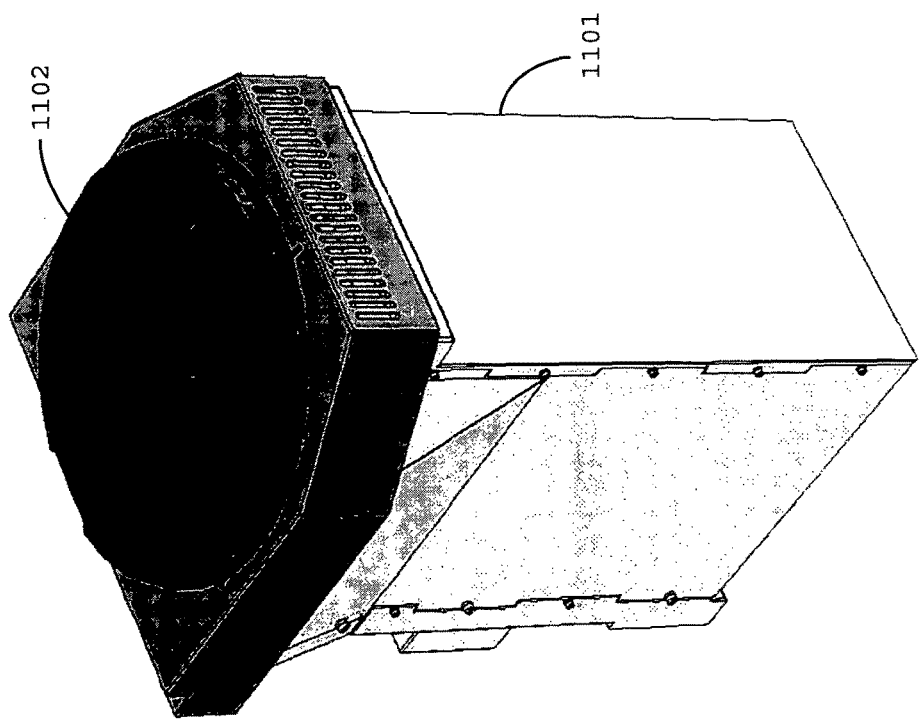
FIG. 11-19 illustrate an illumination module according to an embodiment.
Figure 12:
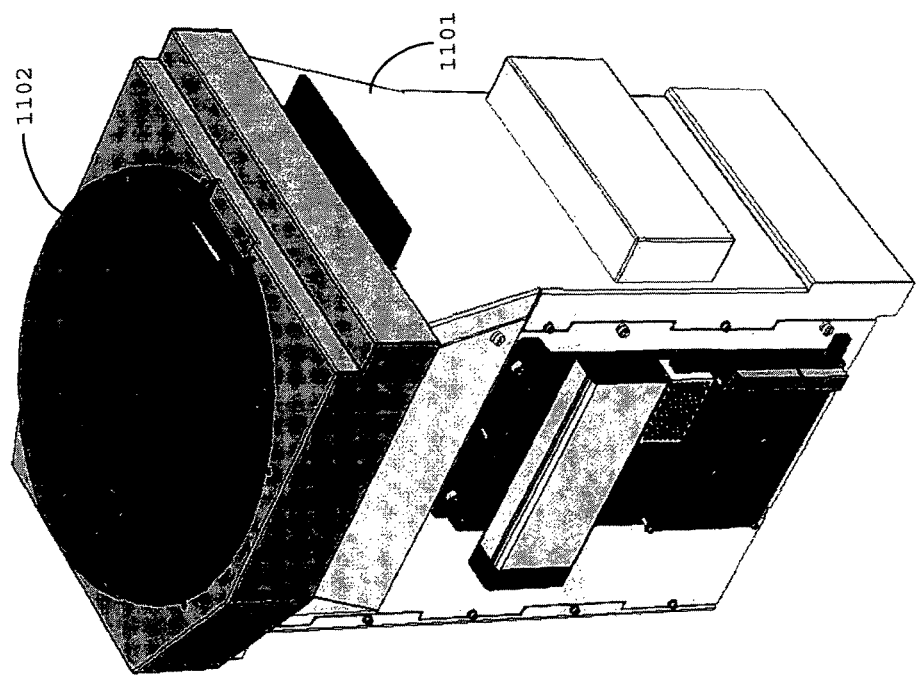
Figure 13:
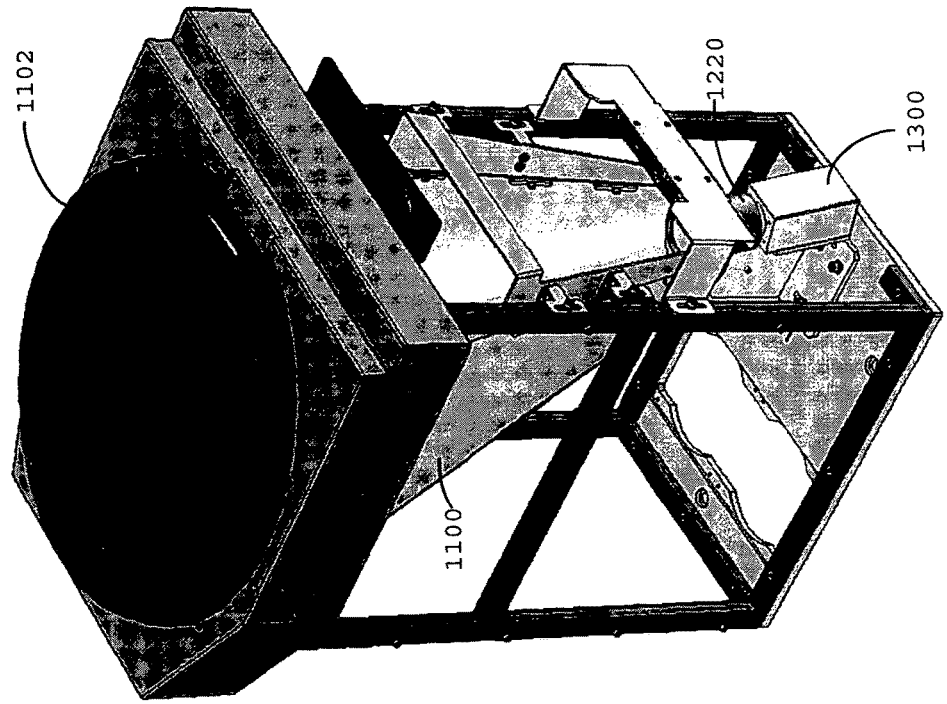
Figure 14:
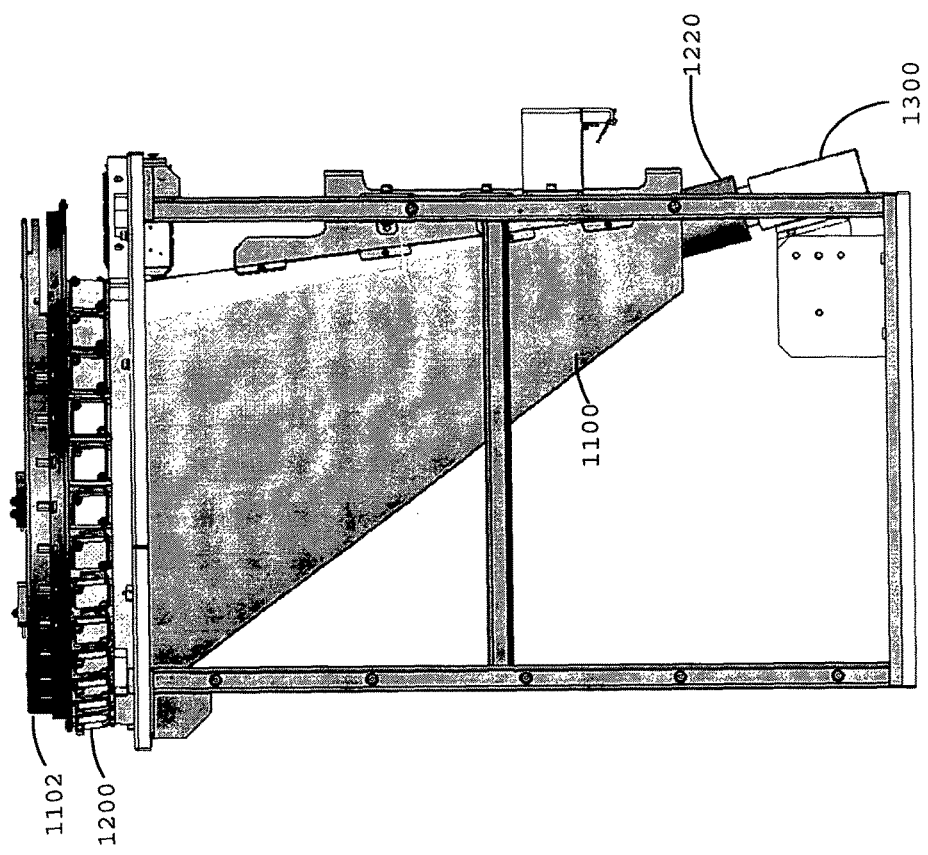
Figure 15:
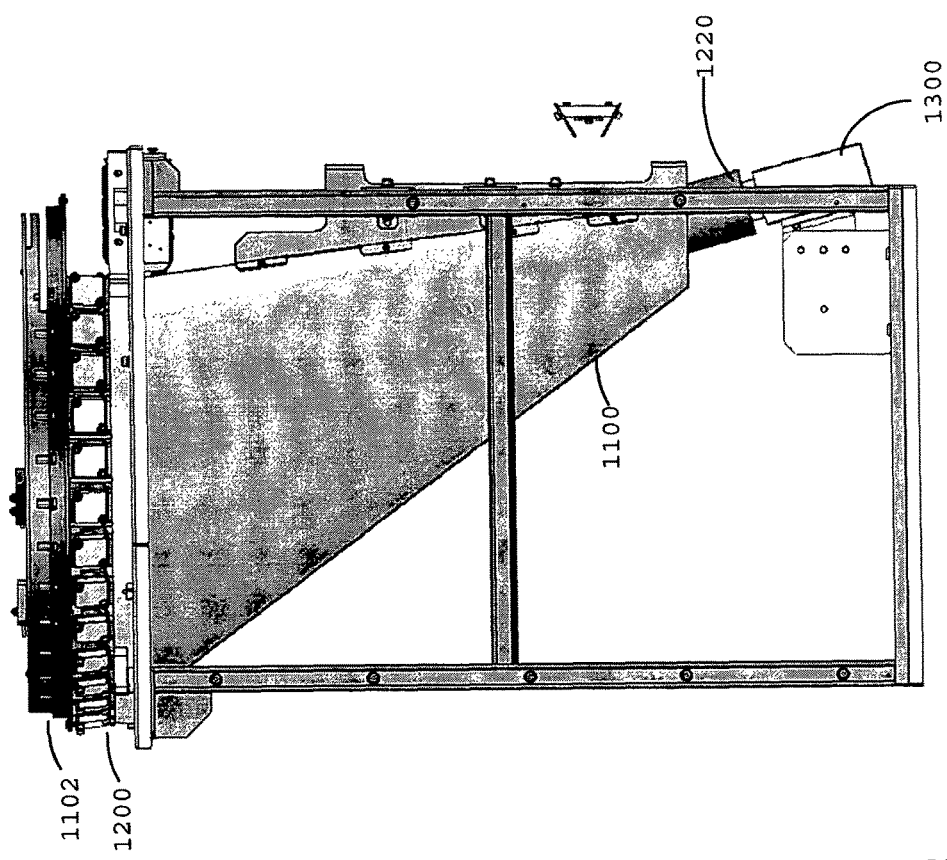
Figure 16:
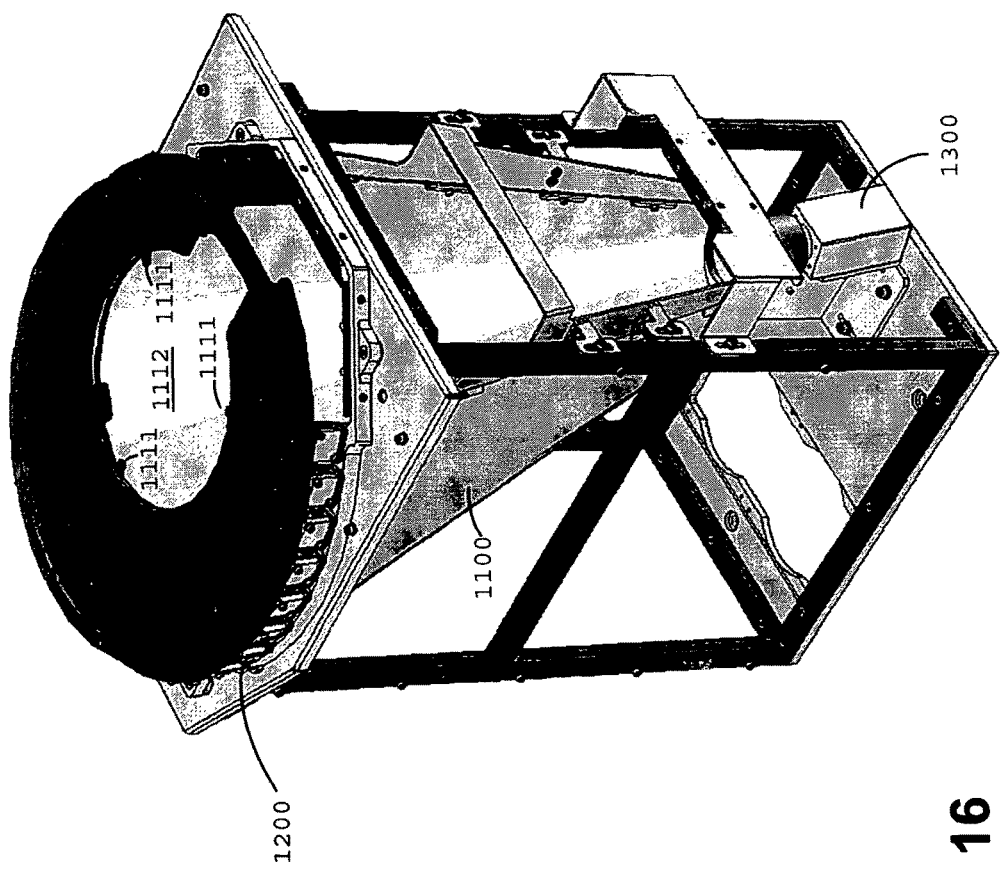
Figure 17:
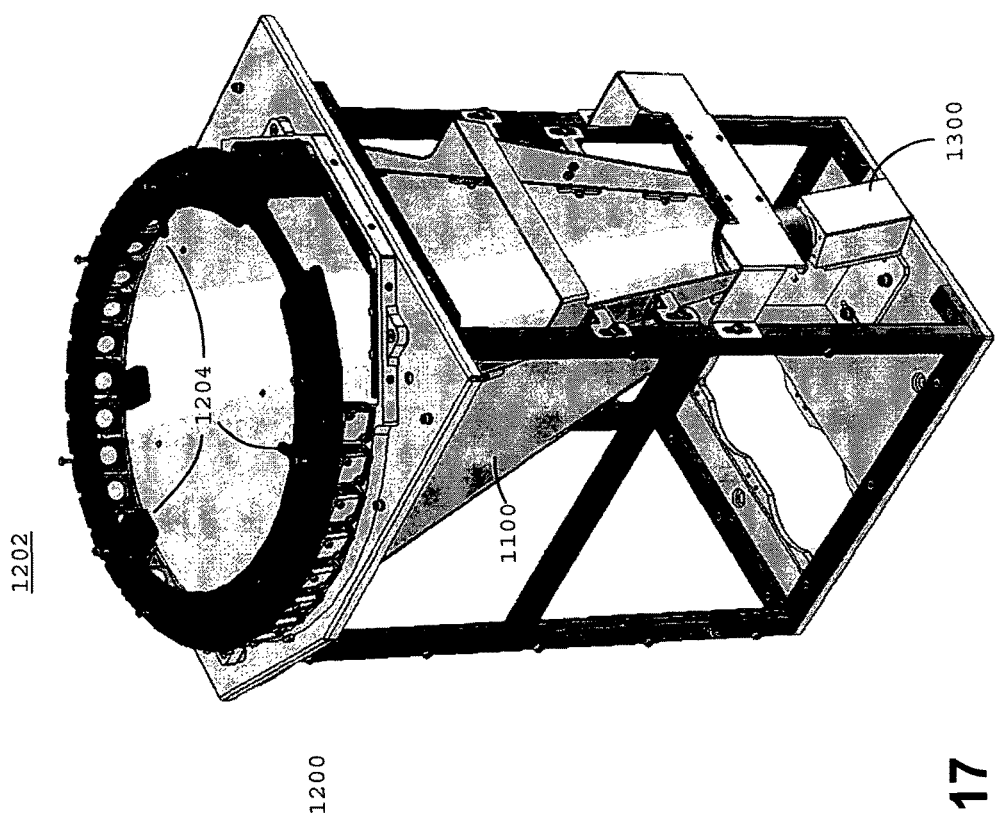
Figure 18:
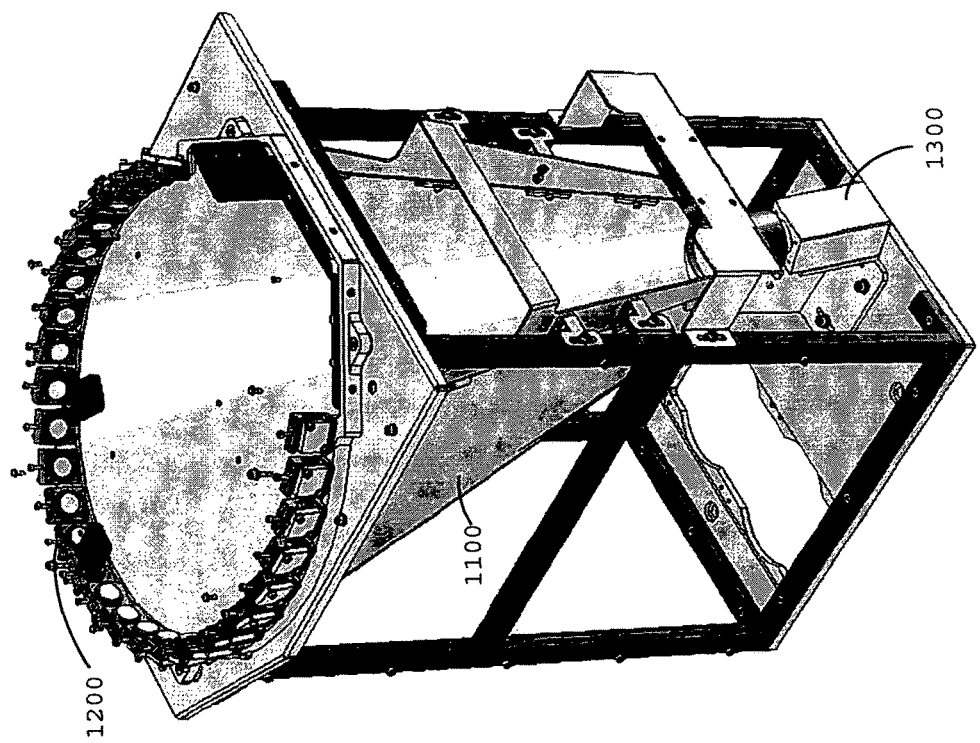

This embodiment is disclosed in FIGS. 11-19. FIGS. 11 and 12 illustrates a housing 1101 of the illumination module and a top cover 1102 of the illumination module. The top cover 1102 has an opening (shown in FIG. 16) on which a wafer is placed. FIG. 13 illustrates top cover 1102, and camera 1300. Camera 1300 is positioned below objective lens 1220 that in turn is positioned below diffusive reflecting curved surface 1100. FIGS. 14 and 15 are side views of camera 1300, objective lens 1220, diffusive reflecting curved surface 1100, darkfield illumination elements 1200 and top cover 1102. FIG. 16 illustrates opening 1112 of top cover 1102 and three supporting elements 1111 that are located near the edge of opening 1112 and support a wafer (not shown) that once placed on supporting elements 1111 can seal opening 1112 or at least almost entirely close the opening. FIG. 16 also illustrates darkfield illumination elements 1200, camera 1300, objective lens 1220 and diffusive reflecting curved surface 1100. FIGS. 17 and 18 illustrate camera 1300, darkfield illumination elements 1200, objective lens 1220, opening 1202 and diffusive reflecting curved surface 1100. It is noted that multiple openings can be defined—at different locations and/or at different heights. For example—FIG. 17 illustrates a larger opening 1202 on which a larger wafer can be supported. It is further noted that a single opening can support wafers of different sizes—if appropriate supporting elements are provided.

Figure 19:
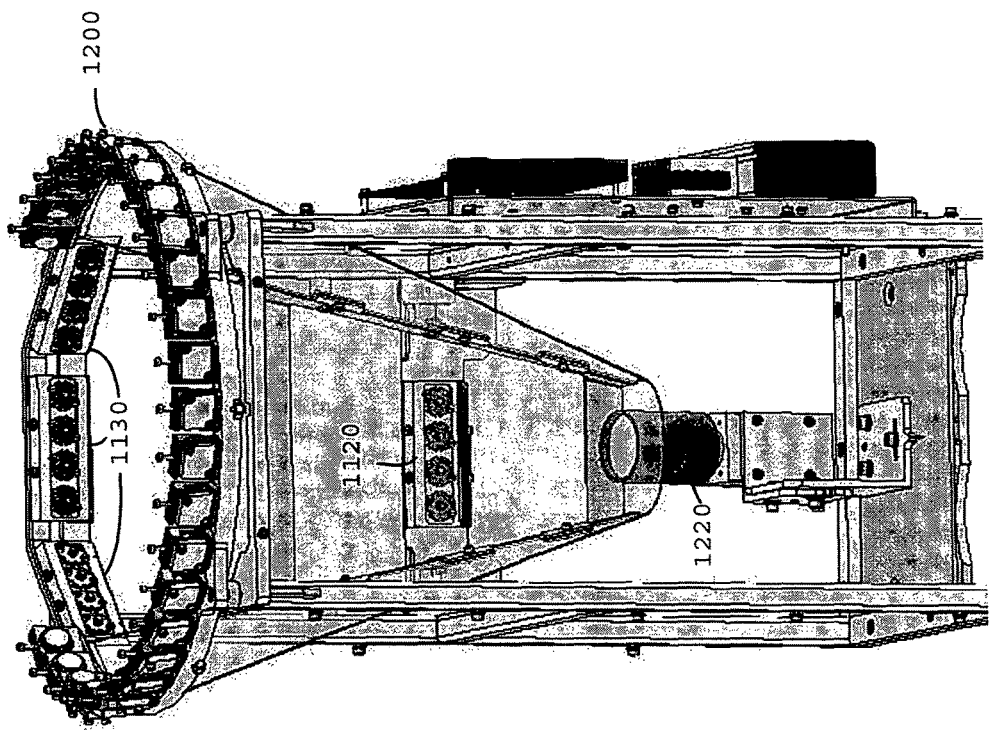

FIG. 19 provides a detailed illustration of the various components of the illumination module.

Diffusive reflecting curved surface 1100 is illuminated by an external illumination source (also referred to as first illumination source) such as illumination elements 1120 and 1130 that do not directly illuminate the wafer.

The diffusive reflecting curved surface 1100 forms a partially open cone. It is tilted in relation to an imaginary axis that is perpendicular to the wafer. The opening in the cone is used for illuminating the diffusive reflecting curved surface 1100 by a first illumination source, In FIG. 19 the first illumination source is shown as including a set of light sources (such as light emitting diodes) that are located below the middle of diffusive reflecting curved surface 1100 as well as three sets of light sources 1130 that are located between the wafer and above diffusive reflecting curved surface 1100. The imaginary axis of diffusive reflecting curved surface 1100 is tilted towards the opening of the cone.

Oblique dark field illumination can be obtained by activating one or more light sources 1200 that are positions between the upper edge of diffusive reflecting curved surface 1100 and the wafer. These light sources 1200 are arranged in a radial formation that corresponds to the radial shape of the upper edge of diffusive reflecting curved surface 1100.

These light sources can be positioned with an inclination of shallow angle relatively to the object plane of the imaging device.

The reflected light from the diffusive surface illuminates the wafer (or another flat object) to create a brightfield image of the object (due to the diffusion the image is not purely a brightfield image).

The darkfield imaging can be suitable for imaging objects such as un-patterned wafers or wafer backside.

Figure 20:
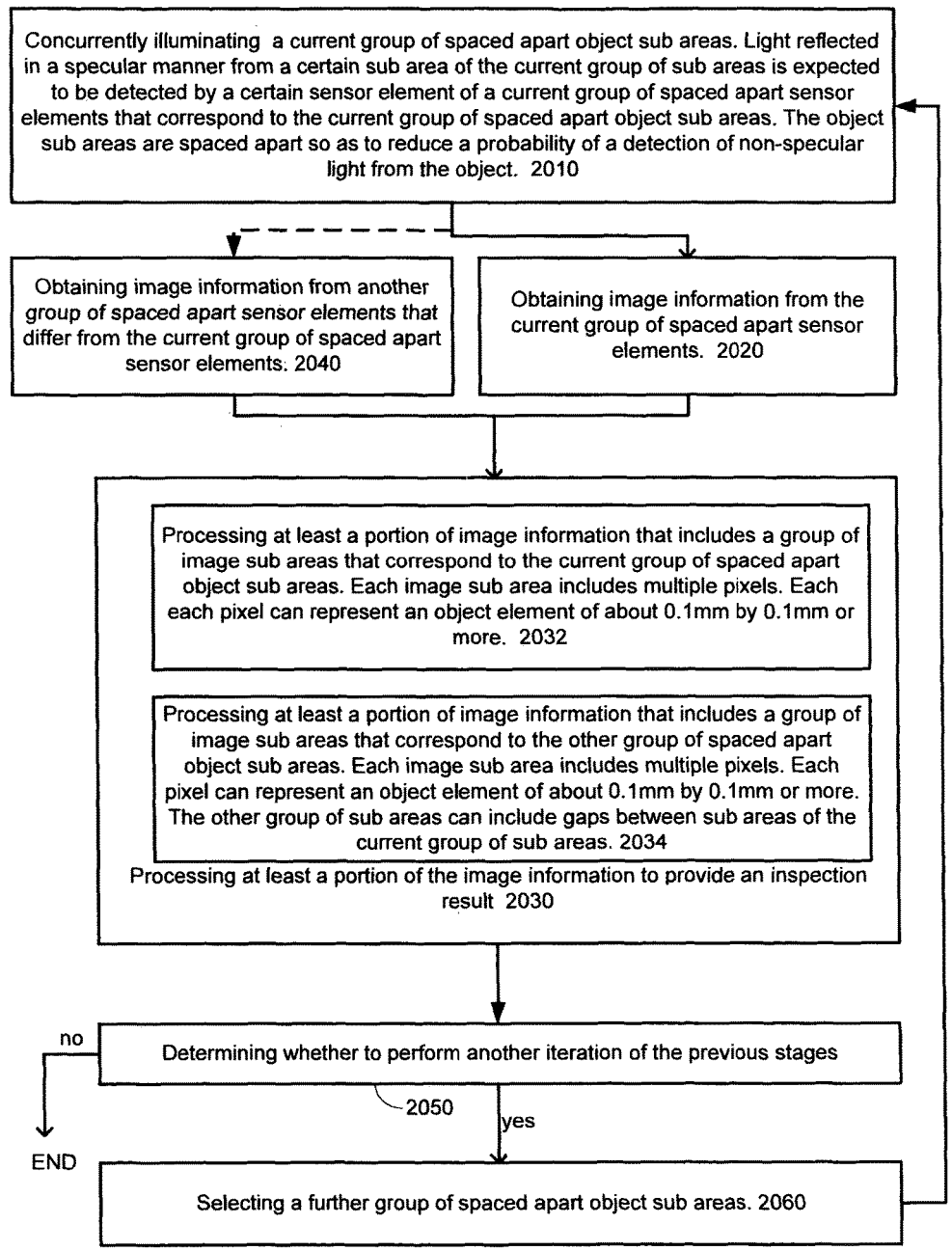

FIG. 20 illustrates method 2000 according to an embodiment of the invention.

Method 2000 starts by stage 2010 of concurrently illuminating a current group of spaced apart object sub areas. Light reflected in a specular manner from a certain sub area of the current group of sub areas is expected to be detected by a certain sensor element of a current group of spaced apart sensor elements that correspond to the current group of spaced apart object sub areas. The object sub areas are spaced apart so as to reduce a probability of a detection of non-specular light from the object. The object sub areas are spaced apart by at least one half a width of a sub area.

Stage 2010 can include activating a current group of spaced apart illumination elements so as to concurrently illuminate the current group of spaced apart object sub areas. These illumination elements can be pixels of LCD screen that is followed by a diffuser. A single illuminating element is illustrated in FIG. 6.

Stage 2010 is followed by stage 2020 of obtaining image information from the current group of spaced apart sensor elements. Stage 2020 can include obtaining image information of an area of the object—the area includes a group of object sub-areas that are specularily illuminated and can include adjacent areas.

Each object sub area ($Ao_i$) can be correlated to an illumination sub area ($Ai_i$) of the illumination device, such that the illuminating sub area ($Ai_i$) illuminates the object sub area ($Ao_i$) by almost solely specular rays relatively to the imaging module. The object sub area ($Ao_i$) is more purely brightfield illuminated and not (or almost not) illuminated by darkfield rays.

There is a small chance that light that has been scattered from an object sub area Aoi will be collected by a sensing element that "covers" area Aoj.

Stage 2020 is followed by stage 2030 of processing at least a portion of the image information to provide an inspection result.

According to an embodiment of the invention stage 3030 includes stage 3032 of processing at least a portion of image information that includes a group of image sub areas that correspond to the current group of spaced apart object sub areas. Each image sub area includes multiple pixels. These pixels can be few of tens of micron wide and even bigger. Each image sub area can include multiple pixels each representing an object element of about 0.1 mm by 0.1 mm or more.

The inspection result can provide an indication of a macro phenomena but this is not necessarily so. The macro phenomena can be macro defects, and the like. The size of the detected macro phenomena is dictated by relatively large size of pixels of an imaging device that obtains the image information. Relatively large pixels can reduce the cost of applying the system.

Stage 2030 can include ignoring image information (by cropping) obtained from object sub-areas that do not belong to the current group of spaced apart object sub-areas. This can include removing (or reducing) dark field information.

Method 2000 can include stage 2040 of obtaining image information from another group of spaced apart sensor elements that differ from the current group of spaced apart sensor elements. This can be viewed as obtaining darkfield information. The other group can represent gaps between members of the current group of spaced apart object sub areas. Thus, while cropped image sections ($Is_i$) represent bright field information other image sections (such as Ign, Igm) represent dark field information. Stage 2040 can be preceded by stage 2010 and can be followed by stage 2030 of processing at least a portion of the image information to provide an inspection result. In this case stage 2030 can include stage 2034 of processing at least a portion of image information that includes a group of image sub areas that correspond to the other group of spaced apart object sub areas. Each image sub area includes multiple pixels. These pixels can be few of tens of micron wide and even bigger. Each image sub area can include multiple pixels each representing an object element of about 0.1 mm by 0.1 mm or more. The other group of sub areas can include gaps between sub areas of the current group of sub areas. These gaps can be smaller than the sub areas of the group of current sub areas, but this is not necessarily so.

Stage 2030 can include applying both stages 2032 and 2034.

Method 2000 can be used to illuminate an entire wafer or at least an entire section of the wafer. Thus, after a current group of spaced apart object sub areas are illuminated a further group of spaced apart object sub areas (referred to as next group of spaced apart object sub areas) is illuminated. The can be repeated until entire object (or an entire section of the object) is illuminated and their relevant image information is processed.

Accordingly, stage 2040 can be followed by stage 2050 of determining whether to perform another iteration of the previous stages (2010, 2020, 2030 and optionally 2040).

Stage 2050 can include determining to perform another iteration of stages 2010, 2020 and 2030—until a predefined portion of the wafer is imaged.

If stage 2050 determines to perform another repetition then it is followed by stage 2060 of selecting a further group of spaced apart object sub areas and jumping to stage 2010. Multiple repetitions of stage 2060 can provide a selection of one group of spaced apart object sub areas after the other until obtaining image information from an entire continuous area of the object. The entire continuous area can be a portion of the wafer or the entire wafer.

During the next iteration of stage 2010, 2020 and 2030 a further group of spaced apart sub areas will be illuminated and image information related to that further group of spaced apart sub areas can be acquired.

If the further group is referred to as the next group of spaced apart sub images then the next iteration of stage 2010 includes concurrently illuminating the next group of spaced apart object sub areas; wherein light reflected in a specular manner from a certain object sub area of the next group of spaced apart object sub areas is expected to be detected by a certain sensor element of a next group of spaced apart sensor elements that correspond to the next group of spaced apart object sub areas; wherein the object sub areas are spaced apart so as to reduce a probability of a detection of non-specular light from the object. The next iteration of stage 2020 will include obtaining image information from the next group of spaced apart sensor elements. The next iteration of stage 2030 will include processing at least a portion of the image information to provide an evaluation of the object.

Stage 2060 can include introducing a mechanical movement between the object and the sensor in order to illuminate sub areas that belong to another section of the wafer.

FIG. 21 illustrates method 2100 according to an embodiment of the invention.

Method 2100 starts by stage 2110 of illuminating a curved diffusive reflecting surface by light beams generated by a first illumination source. The curved diffusive reflecting surface is shaped and positioned so as to direct at least some of the light beams towards the wafer. Such a curved diffusive element reflecting surface is illustrated in FIGS. 11-19. The curved diffusive reflecting surface forms a partially open cone that has an upper opening that is larger than its lower opening. The wafer is placed above the curved diffusive reflecting surface, as illustrated by a round opening of FIG. 16.

Stage 2110 is followed by stage 2120 of collecting, by an imaging device, light beams that were reflected from the wafer. The imaging device is positioned so as to reduce a probability of collecting a reflection of the imaging device.

The imaging device itself can be reflected from the wafer. In order to prevent such reflection the optical axis of the imaging device can be tilted (by a tilt angle that differs from ninety degrees) in relation to the wafer and the curved diffusive reflecting surface is shaped and position so as to direct such reflections outside the objective lens that directs light towards the imaging device. Conveniently, the curved diffusive reflecting surface has an imaginary central axis that is tilted in relation to the wafer by a tile angle that differs from ninety degrees.

Stage 2110 can be preceded by positioned the wafer above the curved diffusive reflecting surface and positioning an objective lens that is followed by the imaging device below the curved diffusive reflecting surface.

Method 2100 can also include stage 2130 of dark field illuminating the wafer. Stage 2130 can be followed by stage 2140 that is analogues to stage 2020 of collecting, by an imaging device, light beams from the wafer.

Method 2100 also includes processing at least some detection signals generated by the imaging device in view of the collected light beams. The processing can include contamination analysis, macro defect detection, and the like.

The mentioned above method can provide low cost inspection of wafers and especially low cost inspection of a backside of a wafer or of an unpatterned wafer.

Variations, modifications, and other implementations of what is described herein will occur to those of ordinary skill in the art without departing from the spirit and the scope of the invention as claimed.

Furthermore, those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A method for macro inspection, the method comprising:
concurrently illuminating a current group of spaced apart object sub areas; wherein light reflected in a specular manner from a certain object sub area of the current group of spaced apart object sub areas is expected to be detected by a certain sensor element of a current group of spaced apart sensor elements that correspond to the current group of spaced apart object sub areas; wherein the spaced apart object sub areas are spaced apart so as to reduce a probability of a detection of non-specular light from the object;
obtaining image information from the current group of spaced apart sensor elements; wherein the obtaining comprises detecting by the certain sensor element the light reflected in the specular manner from the certain object sub area of the current group of spaced apart object sub areas; wherein the image information comprises multiple spaced apart image sub areas; wherein each image sub area comprises multiple pixels; and
processing at least a portion of the image information to provide an inspection result.

2. The method according to claim 1 wherein the object sub areas are spaced apart by at least one half a width of an object sub area.

3. The method according to claim 1 comprising activating a current group of spaced apart illumination elements so as to concurrently illuminate the current group of spaced apart object sub areas.

4. The method according to claim 1 comprising obtaining image information from another group of spaced apart sensor elements that differ from the current group of spaced apart sensor elements.

5. The method according to claim 1 comprising:
selecting a next group of spaced apart object sub areas;
concurrently illuminating the next group of spaced apart object sub areas;
wherein light reflected in a specular manner from a certain sub area of the next group of spaced apart object sub areas is expected to be detected by a certain sensor element of a next group of spaced apart sensor elements that correspond to the next group of spaced apart object sub areas; wherein the object sub areas are spaced apart so as to reduce a probability of a detection of non-specular light from the object;
obtaining image information from the next group of spaced apart sensor elements; and
processing at least a portion of the image information to provide an evaluation of the object.

6. The method according to claim 5 comprising repeating the selection of next group of spaced apart object sub areas until obtaining image information from an entire continuous area of the object.

7. The method according to claim 6 wherein the entire continuous area of the object is a portion of the object; and wherein the method comprises introducing a mechanical movement between the object and the sensor and repeating the stages of concurrently illuminating, obtaining image information and selecting a next group of spaced apart object sub areas until obtaining image information from another entire continuous area of the object.

8. The method according to claim 5 comprising repeating the selection of next group of spaced apart object sub areas until obtaining image information from the entire object.

9. The method according to claim 1 comprising selecting illuminating elements of an LCD screen, and activating the selected elements of the LCD screen so as to illuminate a current group of spaced apart object sub areas.

10. The method according to claim 1 wherein each image sub area comprises multiple pixels each representing an object element of about 0.1 mm by 0.1 mm.

11. The method according to claim 1 comprising obtaining image information by an, imaging system that comprises imaging optics and an imaging sensor; wherein an optical axis of the imaging optics intersects an imaging surface of the imaging sensor at a point that differs from a center of the imaging sensor.

12. The method according to claim 1 comprising selecting illuminating elements of a screen, and activating the selected elements of the screen so as to illuminate a current group of spaced apart object sub areas.

13. The method according to claim 1 wherein the spaced apart object sub areas of the current group of spaced apart object sub areas form a rectangular grid of spaced apart object sub areas.

14. The method according to claim 1 comprising activating a current group of spaced apart illumination elements so as to concurrently illuminate the current group of spaced apart object sub areas; wherein the current group of spaced apart illumination elements belong to a flat illumination unit that is larger than the object.

15. The method according to claim 1 wherein the obtaining image information is executed by an imaging device, and wherein the method comprises comprising preventing the imaging device from being reflected from the wafer.

16. A system for macro inspection, the system comprising:
illumination device configured to concurrently illuminate a current group of spaced apart object sub areas; wherein light reflected in a specular manner from a certain object sub area of the current group of object sub areas is expected to be detected by a certain sensor element of a current group of spaced apart sensor elements that correspond to the current group of spaced apart object sub areas; wherein the object sub areas are spaced apart so as to reduce a probability of a detection of non-specular light from the object;
an imaging device configured to obtain image information from the current group of spaced apart sensor elements; wherein the certain sensor element is configured to detect the light reflected in the specular manner from the certain object sub area of the current group of spaced apart object sub areas; wherein the image information comprises multiple image sub areas, each image sub area comprises multiple pixels; and
a processor configured to process at least a portion of the image information to provide an inspection result.

17. The system according to claim 16 wherein the object sub areas are spaced apart by at least one half a width of an object sub area.

18. The system according to claim 16 wherein the illumination device is configured to activate a current group of spaced apart illumination elements so as to concurrently illuminate the current group of spaced apart object sub areas.

19. The system according to claim 16 configured to obtain image information from another group of spaced apart sensor elements that differ from the current group of spaced apart sensor elements.

20. The system according to claim 16 configured to select a next group of spaced apart object sub areas;
concurrently illuminate the next group of spaced apart object sub areas; wherein light reflected in a specular manner from a certain object sub area of the next group of spaced apart object sub areas is expected to be detected by a certain sensor element of a next group of spaced apart sensor elements that correspond to the next group of spaced apart object sub areas; wherein the object sub areas are spaced apart so as to reduce a probability of a detection of non-specular light from the object;
obtain image information from the next group of spaced apart sensor elements; and
process at least a portion of the image information to provide an evaluation of the object.

21. The system according to claim 20 configured to repeat the selection of next group of spaced apart object sub areas until obtaining image information from an entire continuous area of the object.

22. The system according to claim 14 wherein the entire continuous area of the object is a portion of the object; and wherein the system comprises a mechanical stage for introducing a mechanical movement between the object and the sensor and the system is configured to repeat a concurrent illumination, image obtaining and process of at least a portion of the image information and select a next group of spaced apart object sub areas until obtaining image information from another entire continuous area of the object.

23. The system according to claim 20 comprising repeating the selection of a next group of spaced apart object sub areas until obtaining image information from the entire object.

24. The system according to claim 20 wherein the illuminating device comprises a LCD screen and wherein the device is configured to select illuminating elements of a LCD screen to be activated so as to illuminate a current group of spaced apart object sub areas.

25. The system according to claim 16 wherein the system is configured to illuminate object sub areas that are imaged to provide image sub areas wherein each image sub area comprises multiple pixels each representing an object element of about 0.1 mm by 0.1 mm.

26. The system according to claim 16 wherein the imaging device comprises imaging optics and an imaging sensor; wherein an optical axis of the imaging optics intersects an imaging surface of the imaging sensor at a point that differ from a center of the imaging sensor.

27. The system according to claim 16 wherein the illuminating device comprises a screen, wherein the system is configured to select elements of a screen, and activate the selected elements of the screen so as to illuminate a current group of spaced apart object sub areas.

28. The system according to claim 16 wherein the spaced apart object sub areas of the current group of spaced apart object sub areas form a rectangular grid of spaced apart object sub areas.

29. The system according to claim 16 wherein the illumination device is configured to activate a current group of spaced apart illumination elements so as to concurrently illuminate the current group of spaced apart object sub areas; wherein wherein the current group of spaced apart illumination elements belong to a flat illumination unit that is larger than the object.

* * * * *